(12) United States Patent
Nakashita et al.

(10) Patent No.: US 7,560,002 B2
(45) Date of Patent: Jul. 14, 2009

(54) WATER-ABSORBENT STRUCTURE AND PROCESS FOR MAKING THE SAME

(75) Inventors: Masashi Nakashita, Kagawa-ken (JP); Hisashi Takai, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 58 days.

(21) Appl. No.: 11/507,785

(22) Filed: Aug. 22, 2006

(65) Prior Publication Data

US 2006/0280900 A1    Dec. 14, 2006

Related U.S. Application Data

(62) Division of application No. 10/602,960, filed on Jun. 24, 2003, now Pat. No. 7,135,215.

(30) Foreign Application Priority Data

Jun. 25, 2002    (JP) ............................. 2002-185058

(51) Int. Cl.
    *D04H 1/54*    (2006.01)
    *A61F 13/53*   (2006.01)

(52) U.S. Cl. ...................... 156/62.2; 156/198; 156/221; 156/245; 604/366

(58) Field of Classification Search ................ 156/62.2, 156/198, 221, 245, 305, 308.6; 264/517, 264/109, 121, 122, 126; 604/366, 368, 369, 604/370, 374, 385.101, 385.16; 428/116, 428/311.11

See application file for complete search history.

(56) References Cited

U.S. PATENT DOCUMENTS

| | | | |
|---|---|---|---|
| 4,500,315 A | | 2/1985 | Pieniak et al. |
| 5,098,423 A | * | 3/1992 | Pieniak et al. .......... 604/385.27 |
| 5,277,854 A | * | 1/1994 | Hunt ............................ 264/86 |
| 5,547,747 A | | 8/1996 | Phan et al. |
| 5,643,238 A | | 7/1997 | Baker |
| 2001/0037103 A1 | * | 11/2001 | Onishi ................... 604/385.19 |
| 2003/0104748 A1 | | 6/2003 | Brown et al. |

* cited by examiner

*Primary Examiner*—Richard Crispino
*Assistant Examiner*—Michael A Tolin
(74) *Attorney, Agent, or Firm*—Butzel Long

(57) ABSTRACT

A water-absorbent structure comprises an assembly of thermoplastic synthetic fibers, cellulose-based fibers, super-absorbent polymer and water-pervious sheets wrapping these components together. The assembly is a honeycomb construction having a plurality of through-holes and normally in a compressed state. Upon water permeation into the water-absorbent structure, the super-absorbent polymer is swollen and softened and the assembly is swollen so that the through-holes restore the initial state before the assembly has been compressed.

4 Claims, 5 Drawing Sheets

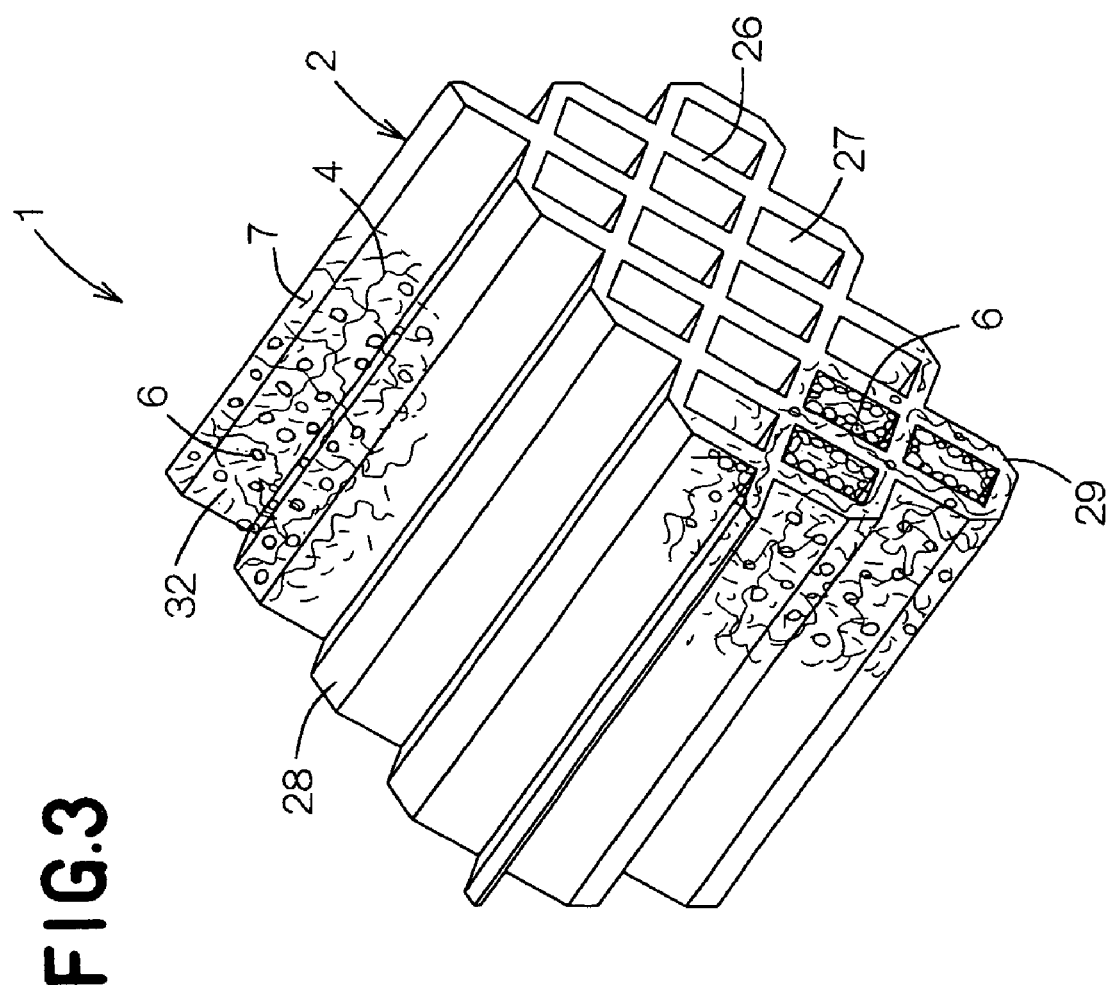

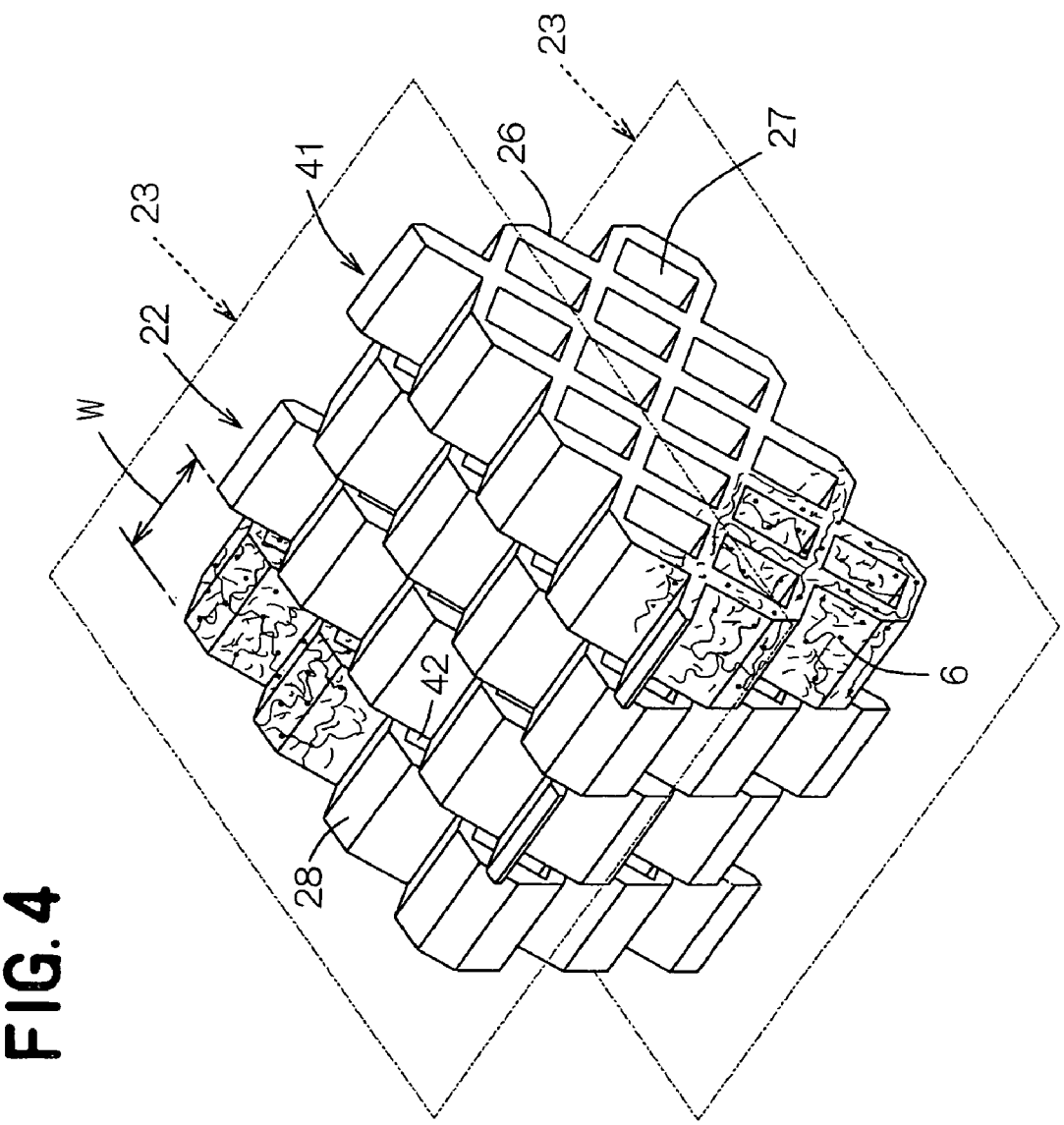

WATER-ABSORBENT STRUCTURE AND PROCESS FOR MAKING THE SAME

RELATED APPLICATIONS

The present application is a divisional application of U.S. patent application Ser. No. 10/602,960, filed Jun. 24, 2003 now U.S. Pat. No. 7,135,215 which claims priority under 35 U.S.C. §119 to Japanese Patent Application No. 2002-185058, filed Jun. 25, 2002.

BACKGROUND OF THE INVENTION

The present invention relates to a water-absorbent structure for various articles requiring a water-absorbing property such as a disposable diaper, a sanitary napkin and disposable wipes and also to a process for making the same.

U.S. Pat. No. 4,500,315 discloses a disposable superthin water-absorbent article. This article comprises a first layer, a second layer and an intermediate layer disposed between these first and second layers. The first layer comprises, in turn, a synthetic fibrous web and a plurality of super-absorbent polymer particles distributed in this web. The second layer is a wad formed by intertwined cellulose fibers or the like contributing to a liquid diffusibility. The intermediate layer also is formed by intertwined cellulose fibers or the like partially contacting with the polymer particles of the first layer. This article is compressed in its thickness direction so as to have a thickness less than half of the thickness before compressed and restores a thickness corresponding to at least 75% of its initial thickness before compressed as the article absorbs liquid such as bodily discharges.

Japanese Patent Application Publication No. 1990-74254A discloses an absorbent pad used in the absorbent article. This absorbent pad comprises a mixture of heat-weldable crimped fibers, fluff pulp and water-absorbent polymer particles. The crimped fibers are heat-welded together to form three-dimensional web formation presenting a mat-like appearance. The absorbent pad is obtained by compressing the fluff pulp and polymer particles in a wetted state together with the crimped fibers and then drying the assembly. The absorbent pad is free from a state of compression as the fluff pulp and the polymer particles absorb water sufficiently to become soft and thereupon the absorbent pad restores its initial mat-like state. After restoration of the initial mat-like state, the crimped fibers become easily deformable and, in consequence, the absorbent pad acquires a compressive elasticity.

In both the article disclosed in U.S. Pat. No. 4,500,315 and the absorbent pad disclosed in Japanese Patent Application Publication, the polymer particles are filled and held in interstices of the fibers. If it is desired to avoid falling off of the polymer particles from the absorbent article or pad, the fiber interstices must be as narrow as possible. As a result, the fiber interstices are choked up as the polymer particles absorb water and swell and a breathability of the absorbent article or pad may be remarkably deteriorated.

SUMMARY OF THE INVENTION

It is an object of the present invention to provide a water-absorbent structure comprising a thermoplastic synthetic fiber assembly containing a water-absorbent material improved so that a desired breathability of the structure is maintained even when super-absorbent polymer contained in the structure absorb water and swell.

According to a first aspect of the invention, there is provided a water-absorbent structure, according to a second aspect of the invention, there is provided a process for making the structure.

The first aspect of the present invention relates to a water-absorbent structure comprising a panel-shaped assembly of thermoplastic synthetic fibers having upper and lower surfaces extending in parallel to each other, cellulose-based fibers and super-absorbent polymer adapted to be swollen as the polymer absorbs water both contained in the assembly of the thermoplastic synthetic fibers served as a water-absorbing materials in which at least one of the upper and lower surfaces is wrapped with water-pervious sheets.

According to the invention, the assembly is in the form of a honeycomb construction adapted to be elastically compressed in a thickness direction and has a plurality of through-holes extending parallel to one another in a direction parallel to the upper and lower surfaces, each of the through-holes has a cross-sectional dimension larger than any one of interstices of the thermoplastic synthetic fibers in the assembly. The assembly is normally kept in a state compressed in the thickness direction with the through-holes being flattened and adapted to be elastically swollen in the thickness direction so that the flattened through-holes are restored to the initial cross-sectional shape thereof as the super-absorbent polymer absorbs water and is swollen.

The invention on the first aspect includes the following embodiments.

The super-absorbent polymer is provided in particulate or fibrous form.

The assembly comprises a plurality of honeycomb thin leaves placed upon one another in a transverse direction in which the through-holes extend, each of the honeycomb thin leaves have a width of 3 to 30 mm as measured in the transverse direction.

The through-holes in each pair of the thin leaves adjacent to each other are at least partially connected.

The thermoplastic synthetic fibers are of crimped-type.

The assembly, the cellulose-based fibers and the super-absorbent polymer are mixed at a ratio of 5-80 wt %:5-60 wt %:10-80 wt %.

A cross-sectional shape of the through-hole is a substantially rectangle and one of diagonals of the rectangle is substantially in coincidence with the thickness direction.

The assembly includes at least two through-holes aligned in the thickness direction.

The second aspect of the invention relates to a process for making a water-absorbent structure comprising a panel-shaped assembly of thermoplastic synthetic fibers having upper and lower surfaces extending in parallel to each other, cellulose-based fibers and super-absorbent polymer adapted to be swollen after absorption of water both contained in the assembly of the thermoplastic synthetic fibers served as water-absorbing materials in which at least one of the upper and lower surfaces is wrapped with water-pervious sheets.

According to the invention, the assembly is in the form of a honeycomb construction adapted to be elastically compressed in a thickness direction and has a plurality of through-holes extending parallel to one another in a direction parallel to the upper and lower surfaces, each of the through-holes has a cross-sectional dimension larger than any one of interstices of the thermoplastic synthetic fibers in the assembly. The process comprises steps of compressing the assembly in the thickness direction while the water absorbing materials are in a wetted condition so that the through-holes are flattened, drying the water absorbing materials so as to maintain the assembly in a compressed state and wrapping at least one of the upper and lower surfaces with the water-pervious sheets before or after the step of compressing.

The invention on its second aspect includes the following embodiments.

The super-absorbent polymer is provided in particulate or fibrous form.

The process further comprises steps of feeding a mixture of the thermoplastic synthetic fibers, the cellulose-based fibers and the super-absorbent polymer into a molding die and welding the thermoplastic synthetic fibers at crossways thereof within the molding die under heating to obtain the assembly.

The assembly includes at least two through-holes aligned in the thickness direction.

BRIEF DESCRIPTION OF THE DRAWINGS

FIG. 3 is a perspective view showing the water-absorbent structure as after it has absorbed water;

FIG. 4 is a view similar to FIG. 2 showing another embodiment of the stock panel.

DETAILED DESCRIPTION OF THE PREFERRED EMBODIMENTS

Details of a water-absorbent structure and a process for making the same according to the present invention will be more fully understood from the description given hereunder with reference to the accompanying drawings.

Figure 1:
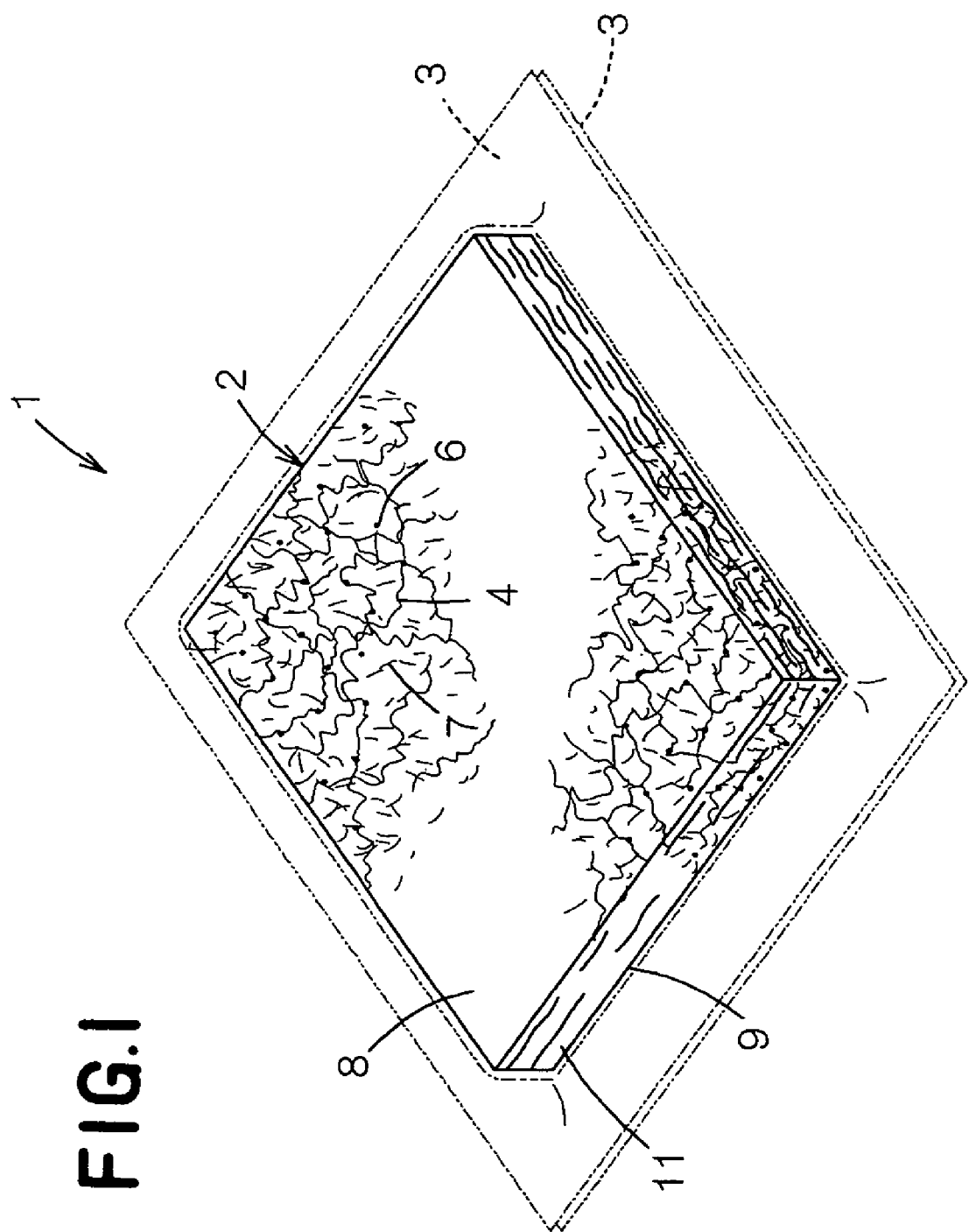
FIG. 1 is a perspective view showing a water-absorbent structure.

A water-absorbent structure 1 shown in FIG. 1 in a perspective view comprises a panel-like core 2 and cover sheets 3 for the core 2. The cover sheets 3 are indicated by imaginary lines. The core 2 comprises a mixture of thermoplastic synthetic fibers 4, super-absorbent polymer particles 6 and fluff pulp 7 compressed together and has an upper surface 8, a lower surface 9 and a peripheral side surface 11. The sheets 3 cover the core 2 on its upper, lower and side surfaces 8, 9, 11 to prevent the core 2 from getting out of its shape and simultaneously to prevent the polymer particles 6 and the fluff pulp 7 from falling off out of the core 2. The sheets 3 are water-pervious at least in a region covering the upper surface 8 of the core 2 and water-pervious or water-impervious in a region covering the lower surface 9 and the side surface 11 of the core 2. In the illustrated embodiment, the core 2 is entirely covered with a pair of water-pervious cover sheets 3.

Figure 2A:
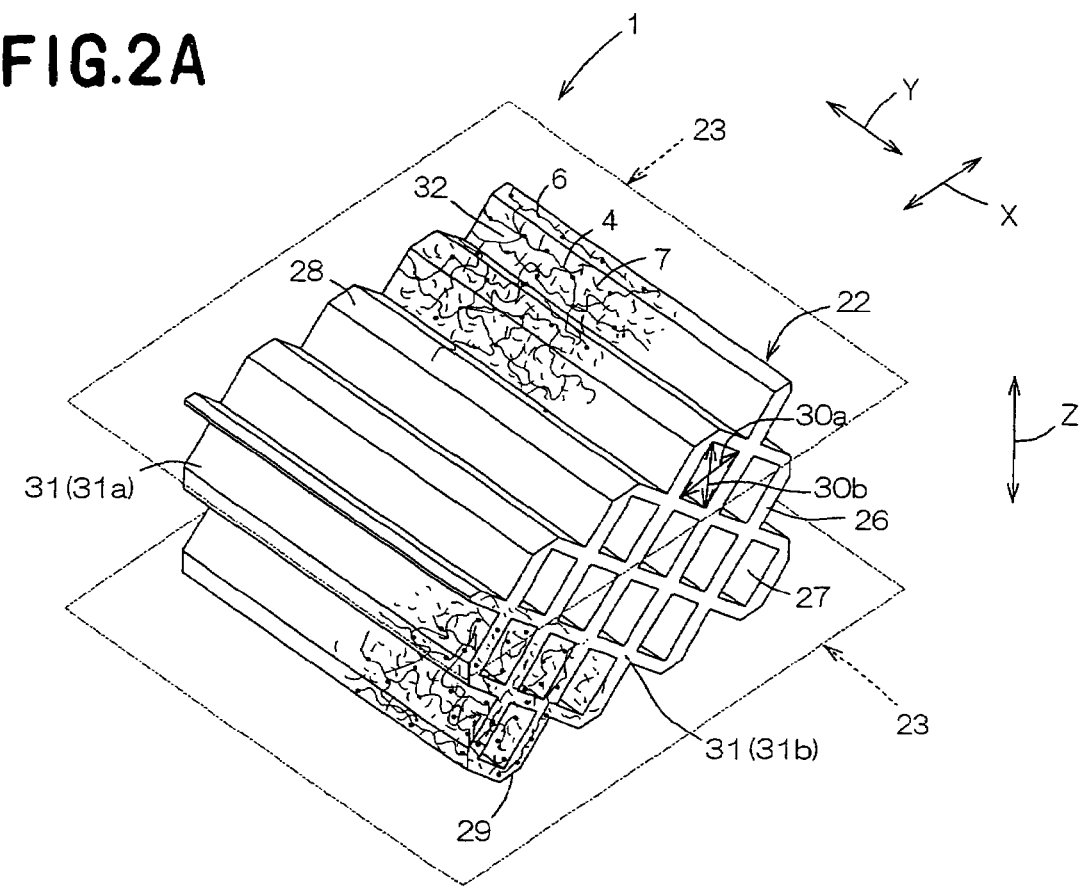
FIG. 2A is a perspective view showing a stock panel and stock sheets.
Figure 2B:
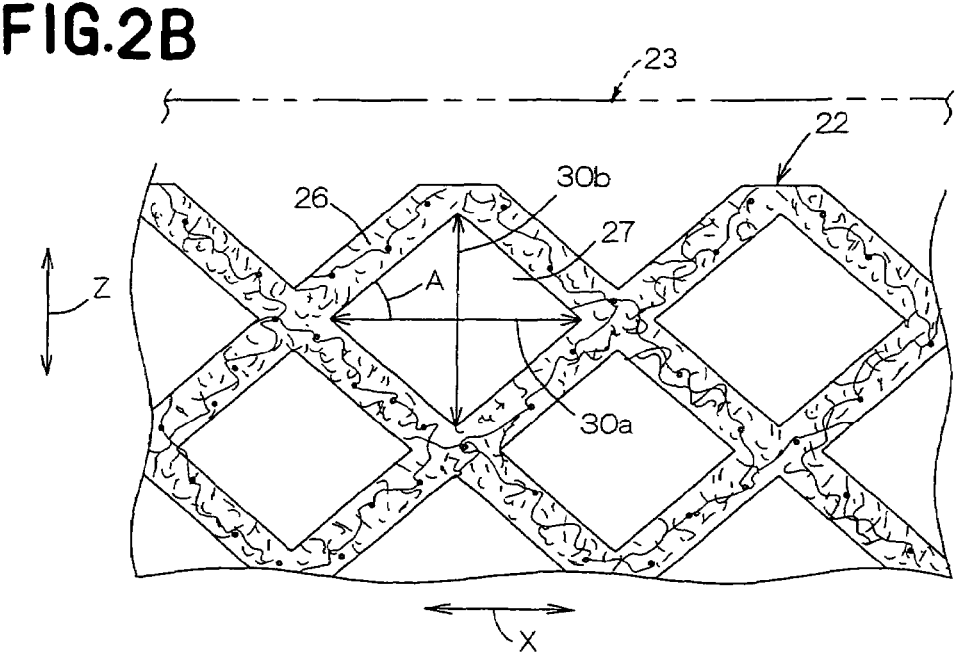
FIG. 2B is a scale-enlarged diagram illustrating a part of FIG. 2A.

FIG. 2A is a perspective view showing a stock panel 22 and stock sheets 23 used for the water-absorbent structure 1 and FIG. 2B is a scale-enlarged diagram illustrating a part of FIG. 2A. In both FIG. 2A and FIG. 2B, the stock sheets 23 are indicated by imaginary lines. The stock panel 22 is of a honeycomb structure in which an assembly of the thermoplastic synthetic fibers 4, the polymer particles 6 and the fluff pulp 7 both scattered in the assembly of fibers form partition walls 26 and define a plurality of through-holes 27. The stock panel 22 has in addition to upper and lower surfaces 28, 29 extending in parallel to each other, side surfaces 31. There are ups and downs repeated in a direction indicated by an arrow X on the upper and lower surfaces 28, 29, each of ups and downs extends in a direction indicated by an arrow Y orthogonal to the direction X. The side surfaces 31 include a pair of side surfaces 31a on which ups and downs are repeated in a direction Z orthogonal to the direction X as well as to the direction Y and a pair of side surfaces 31b on which the through-holes 27 are exposed. The through-holes 27 extend parallel to one another in a direction parallel to the upper and lower surfaces 28, 29 between these upper and lower surfaces 28, 29. Ends of the respective through-holes 27 are exposed in the side surfaces 31b. The through-holes 27 are arranged between the upper and lower surfaces 28, 29 so that at least two through-holes 27 are aligned in the direction Z. While a cross-sectional shape of the through-hole 27 in the stock panel 22 is not specified, a preferred shape thereof is a parallelogram defined by a pair of diagonals 30a, 30b as seen in FIG. 2B. The diagonal 30a, one of these two diagonals, extends in the direction X preferably at an angle A of 15 to 45°, more preferably of 30 to 45° with respect to a pair of opposite sides of the parallelogram and the other diagonal 30b extends in the direction Z, i.e., between the upper and lower surfaces 28, 29. In other words, the partition walls 26 are slanted at the angle A of 15 to 45° with respect to the horizontal extending in the direction X. The stock panel 22 preferably has a basis weight in a range of 300 to 3,000 g/m², of which the thermoplastic synthetic fibers 4 occupy 5 to 80 wt %, the super-absorbent polymer particles 6 occupy 10 to 80 wt % and the fluff pulp 7 occupies 5 to 60 wt %.

The thermoplastic synthetic fibers 4 constituting the stock panel 22 are intertwined and/or heat-welded together to form a fibrous assembly having a three-dimensional web formation, the polymer particles 6 and the fluff pulp 7 are scattered in interstices 32 of the fibers 4. These interstices 32 are significantly smaller than the through-holes 27. The thermoplastic synthetic fibers 4 have a fineness in a range of 1 to 20 dtx and may be selected from the group including short fibers, long fibers, conjugated fibers or crimped conjugated fibers of material which is water-resistant to retain its elasticity, for example, polyethylene, polypropylene, nylon or polyester.

The through-holes 27 in the stock panel 22 are dimensioned so that the through-holes 27 may occupy 10 to 90% of an area on each of the side surfaces 31b and each of the through-holes 27 may have an open area sufficiently large to contain therein at least in order of 10 interstices 32 of the fibers 4.

The stock sheet 23 may be formed by a tissue paper, a nonwoven fabric, a perforated plastic film or the like when it should be water-pervious and may be formed by a water-repellent nonwoven or woven fabric, a plastic film or the like when it should be water-impervious.

The stock panel 22 formed in this manner is subjected independently or together with the stock sheets 23 to water spray until a moisture-content of the polymer particles 6 reaches 5 to 20 wt %. After the polymer particles 6 has absorbed water to be softened, the stock panel 22 is compressed in its thickness direction, i.e., the direction Z to a thickness at which the through-holes 27 are flattened and then dried in a compressed state. The compression elastically deforms the assembly of the thermoplastic synthetic fibers 4 having the three-dimensional web formation so that the component fibers 4 may come close to one another. The thermoplastic synthetic fibers 4 lying adjacent to one another are bonded to one another primarily under an adhesive force of the polymer particles 6 softened in a jelly-like state and mechanical intertwining with the fluff pulp 7. When the polymer particles 6 and the fluff pulp 7 are dried, these thermoplastic synthetic fibers 4, the polymer particles 6 and the fluff pulp 7 integrally become rigid and are kept in a compressed state. Before or after, preferably before compressed, the stock panel 22 is wrapped with the stock sheets 23 and the stock panel 22 having been wrapped with the stock sheets 23 will be integrated with the stock panel 22 after compressed. The stock panel 22 integrated with the stock sheets 23 in this manner forms the water-absorbent structure 1 of FIG. 1. If the through-holes 27 are regularly arranged in the direction X as well as in the direction Z and the partition walls 26 are formed substantially in a uniform thickness as seen in the illustrated embodiment, the stock panel 22 will have a substantially uniform thickness after compressed. Since each of the through-holes 27 has a rectangular, more preferably parallelogrammic cross-section in which one diagonal 30b of two diagonals 30 extends in the direction Z, each of the partition walls 26 obliquely extends with respect to the direction Z and is substantially flattened in the direction Z as the stock panel 22 is compressed in the direction Z. The partition walls 26 are never buckled even under a compressive force in the direction Z because the partition walls 26 does not extend in the direction Z.

FIG. 3 is a perspective view showing the water-absorbent structure 1 after the absorption of water. In FIG. 3, the cover sheets 3 are not illustrated and only the core 2 is illustrated. The water-absorbent structure 1 is adapted to absorb an amount of water permeating through the cover sheets 3 thereinto by the polymer particles 6 and the fluff pulp 7. The polymer particles 6 are swollen and softened as these particles 6 absorb water and the fluff pulp 7 also is softened as it absorbs water. Consequently the thermoplastic synthetic fibers 4 are now free from immobilization by these polymer particles 6 and the fluff pulp 7. Specifically, the fibers 4 having been elastically deformed in the compressed core 2 are now able to move so as to be restored to the state prior to compression and swelling of the polymer particles 6 scattered in the interstices of the fibers 4 enhances enlargement of the interstices 32 to the initial state prior to compression. Simultaneously, the partition walls 26 having been deformed to flatten the through-holes 27 can elastically move so as to restore the through-holes 27 to the initial shape in the stock panel 22. A relatively large amount of the polymer particles 6 may be distributed along respective crossways of the partition walls 26 and in the vicinity of these crossways to promote the partition walls 26 to rise from the collapsed state and to extend obliquely with respect to the direction Z as these particles 6 absorb water and swell. As the partition walls 26 moves to extend obliquely with respect to the direction Z, the core 2 swells toward its upper and lower surfaces 28, 29, i.e., in the direction Z as illustrated in FIG. 3 and the assembly of the thermoplastic synthetic fibers 4 restores its honeycomb construction illustrated in FIG. 2.

In the water-absorbent structure 1, a variation in the thickness thereof between before and after water-absorption depends on its variation due to swelling of the polymer particles 6 and its variation due to restoration of the honeycomb construction. In the core 2 illustrated in FIG. 3, the partition walls 26 forming the stock panel 22 and the through-holes 27 reappear as seen in FIG. 2. In the core 2, the polymer particles 6 are swollen and a part of them are inside the through-holes 27 out of the partition walls 26 in a swollen state. However, the through-holes 27 have a sufficient large cross-sectional dimension to prevent the through-holes 27 from being clogged up by the swollen polymer particles 6. In the water-absorbent structure 1 of FIG. 3 in which the honeycomb construction has restored its initial state, a plurality of through-holes 27 extend parallel to one another in the direction parallel to the upper and lower surfaces 28, 29. With the through-holes 27, even if the interstices 32 of the thermoplastic synthetic fibers 4 in the core 2 are filled with the swollen polymer particles 6, the water-absorbent structure 1 maintains a high breathability. Even if the initial water absorption by the water-absorbent structure 1 causes the polymer particles 6 to form a gel block, the amount of water permeating thereafter into the water-absorbent structure 1 can spread via the through-holes 27 downward as well as laterally into the core 2 and can be absorbed by the polymer particles 6 even at the corners of the core 2. In this way, substantially all of the polymer particles 6 can be effectively utilized. The water-absorbent structure 1 in the state as shown in FIG. 1 can be elastically compressed in its thickness direction so that the partition walls 26 themselves reduce the interstices 32 of the fibers 4 and the structure 1 as a whole can be elastically compressed so as to flatten the through-holes 27.

FIG. 2 is a perspective view showing the stock panel 22 and the stock sheets 23 constituting the water-absorbent structure 1 in a manner different from the manner shown in FIG. 2. The stock sheets 23 are indicated by imaginary lines. In this case, a plurality of honeycomb thin leaves 41 having the same composition and construction as the stock panel 22 of FIG. 2 are used. Each of the thin leaves 41 has the partition walls 26 and a plurality of through-holes 27 defined by these partition walls 26 and preferably has a width W of 5 to 50 mm in the direction in which the through-holes 27 extend. Each pair of the thin leaves 41 adjacent to each other so that the partition walls 26 of the one thin leaf 41 and the partition walls 41 of the other thin leaf 41 are in conformity with each other or so that the partition walls 26 of the one thin leaf 41 block a part of the partition walls 26 of the other thin leaf 41. That is, the through-holes 27 of the one thin leaf 41 are at least partially connected to the through-holes 27 of the other thin leaf 41. Similar to those of FIG. 2, the stock panel 22 and the stock sheets 23 are compressed together to form the water-absorbent structure 1.

Use of the thin leaves 41 in the manner as illustrated in FIG. 4 allows a relatively large water-absorbent structure 1 to be made. Furthermore, when this water-absorbent structure 1 absorbs water and swells, a part 42 of the through-holes 27 is exposed on the upper surface 28 as illustrated in FIG. 4 and the amount of water permeating into the structure 1 after swollen can flow through the part 42 downward into the structure 1 and easily come in contact with the polymer particles 6 lying in the lower region of the structure 1.

Figure 5:
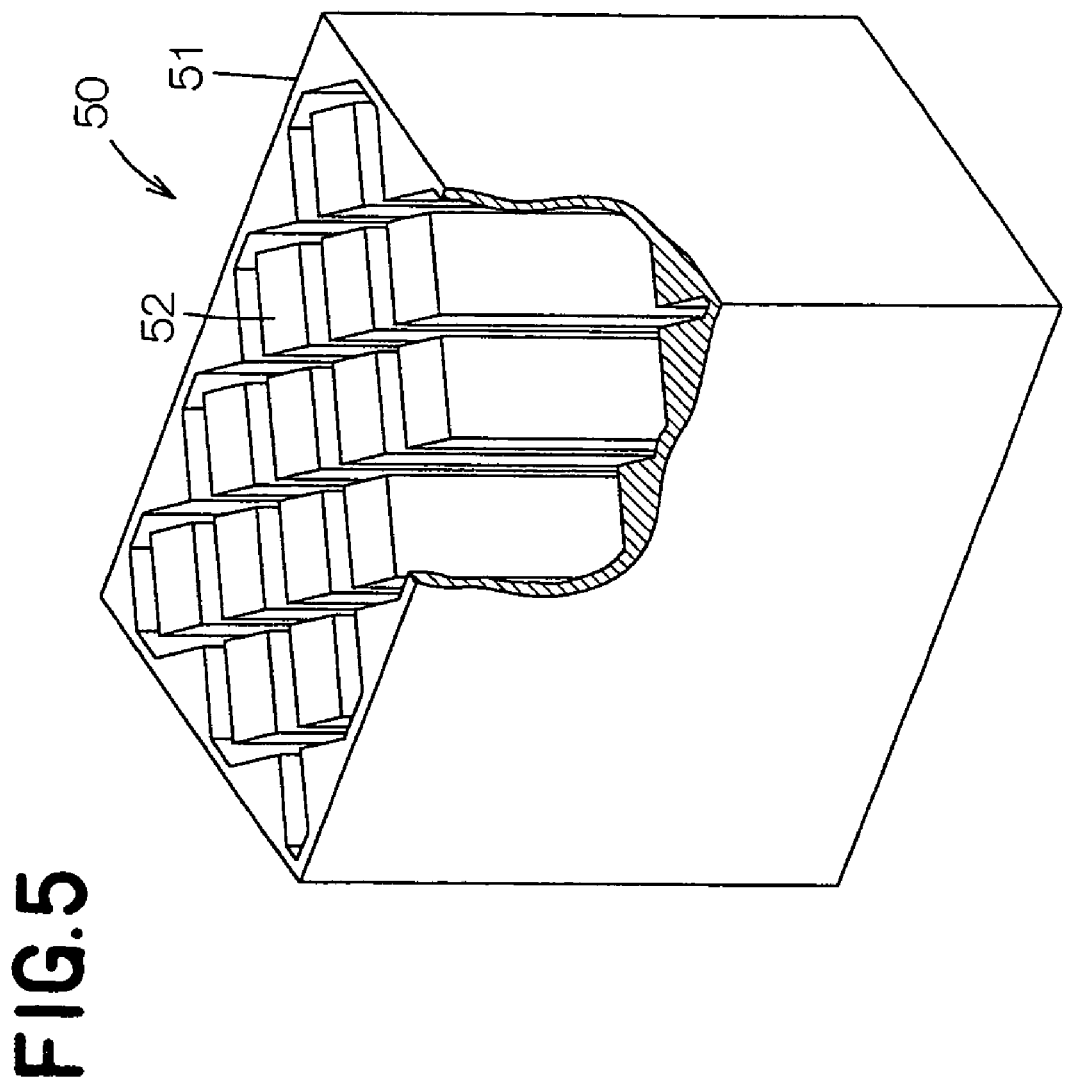
FIG. 5 is a partially cutaway perspective view showing a molding die used to mold the stock panel.

FIG. 5 is a partially cutaway perspective view showing a molding die 50 used to obtain the stock panel 22 as illustrated in FIGS. 2 and 4. The molding die 50 comprises a box-like container 51 and a plurality of square pins 52 rising from within the container 51. The thermoplastic synthetic fibers 4, the super-absorbent polymer particles 6 and the fluff pulp 7 are mixed in a predetermined proportion and fed under the effect of air stream into the container 51. Then the container 51 is heated or the mixture including the fibers is subjected to hot air blast so that the thermoplastic synthetic fibers 4 are welded one another at cross-points thereof to form the three-dimensional web formation and at the same time to scatter the polymer particles 6 and the fluff pulp 7 in this web formation. The assembly of the thermoplastic synthetic fibers 4 may be taken out from the molding die 50 to obtain the stock panel 22 of FIG. 2, which has the through-holes 27 having the shapes corresponding to the pins 52. In the process for making the stock panel 22 in this manner, the thermoplastic synthetic fibers 4 having a length of 5 to 50 mm, more preferably of 5 to 30 mm may be used to obtain the stock panel 22 in which the fiber orientation is relatively simple, the fibers 4, the polymer particles 6 and the fluff pulp 7 are rather uniformly mixed with one another.

Without departing from the scope of the invention, the super-absorbent polymer particles 6 may be replaced by a fibrous super-absorbent polymer. It is also possible to use a tissue paper as the stock sheets 23 serving to wrap the stock panel 22 and to cover this tissue paper with a nonwoven fabric or a perforated plastic film from above. The upper surface 28 and/or the lower surface 29 of the stock panel 22 may be flat instead of those repeating ups and downs. The water-absorbent structure 1 according to the invention may be directly used as water-absorbent product such as a wet wipes or a water-absorbent material or a part thereof used in a disposable wearing article for absorption and containment of body fluids such as a disposable diaper or a sanitary napkin.

The water-absorbent structure according to this invention is in the form of honeycomb construction in which the fibrous assembly containing the super-absorbent polymer scattered therein and normally in a compressed state. The honeycomb construction is restored as the super-absorbent polymer is swollen and softened after absorption of water. This feature allows the water-absorbent structure to maintain the desired breathability and the compressive elasticity.

What is claimed is:

1. Process for making a water-absorbent structure comprising a panel-shaped assembly of thermoplastic synthetic fibers having upper and lower surfaces extending in parallel to each other, cellulose-based fibers and super-absorbent polymer adapted to be swollen after absorption of water both contained in said assembly of said thermoplastic synthetic fibers served as water-absorbing materials wherein at least one of said upper and lower surfaces is wrapped with water-pervious sheets, said assembly comprising a honeycomb construction which is monolithically formed from the thermoplastic synthetic fibers, the cellulose-based fibers and the super-absorbent polymer and having a plurality of through-holes extending parallel to one another in a direction parallel to said upper and lower surfaces, each of said through-holes having a cross-sectional dimension larger than any one of interstices of said thermoplastic synthetic fibers in said honeycomb assembly, said honeycomb assembly being elastically compressible in a thickness direction which is aligned with diagonals of said through-holes and extends between said upper and lower surfaces of said panel-shaped assembly, said process comprises the steps of:

compressing said assembly in said thickness direction while said water absorbing materials are in a wetted condition so that said through-holes are flattened;

drying said water absorbing materials so as to maintain said assembly in a compressed state; and wrapping at least one of said upper and lower surfaces with said water-pervious sheets before or after said step of compressing.

2. The process according to claim 1, wherein said super-absorbent polymer is provided in a particulate or fibrous form.

3. The process according to claim 1, wherein said process further comprises the steps of feeding a mixture of said thermoplastic synthetic fibers, said cellulose-based fibers and said super-absorbent polymer into a molding die and welding said thermoplastic synthetic fibers at crossways thereof within said molding die under heating to obtain said assembly.

4. The process according to claim 1, wherein said assembly includes at least two said through-holes aligned in said thickness direction.

* * * * *